United States Patent [19]

Deschler et al.

[11] Patent Number: 5,049,690
[45] Date of Patent: Sep. 17, 1991

[54] N,N'-DISUBSTITUTED AND N,N,N'-/N,N', N'-TRISUBSTITUTED THIOUREAS AND METHOD OF THEIR PREPARATION (II)

[75] Inventors: Ulrich Deschler, Brasschaat, Belgium; Peter Panster, Rodenbach; Peter Kleinschmit, Hanau, both of Fed. Rep. of Germany

[73] Assignee: Degussa Aktiengesellschaft, Fed. Rep. of Germany

[21] Appl. No.: 556,544

[22] Filed: Jul. 24, 1990

[30] Foreign Application Priority Data

Jul. 31, 1989 [DE] Fed. Rep. of Germany ....... 3925356

[51] Int. Cl.$^5$ .............................. C07F 7/10
[52] U.S. Cl. ................................. 556/421
[58] Field of Search ......................... 556/421

[56] References Cited

U.S. PATENT DOCUMENTS

| | | | |
|---|---|---|---|
| 4,645,846 | 2/1987 | DePasquale et al. | 556/421 X |
| 4,851,492 | 7/1989 | Panster et al. | 556/421 X |
| 4,855,470 | 8/1989 | Panster et al. | 556/421 |

FOREIGN PATENT DOCUMENTS

| | | | |
|---|---|---|---|
| 3821465 | 12/1989 | Fed. Rep. of Germany | 556/421 |
| 0379580 | 7/1973 | U.S.S.R. | 556/421 |

*Primary Examiner*—Paul F. Shaver
*Attorney, Agent, or Firm*—Cushman, Darby & Cushman

[57] ABSTRACT

N,N'-disubstituted or N,N,N'- or N, N', N'-trisubstituted thioureas with additional organyloxysilyl function and tertiary amine function of the general formula

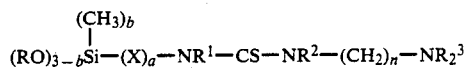

These compounds are prepared as follows:
a) Aminoorganylsilanes of the general formula

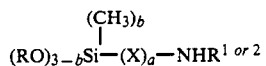

are reacted in an organic, inert solvent with carbon disulfide,
b) The dithiocarbamates formed thereby having the general formula:

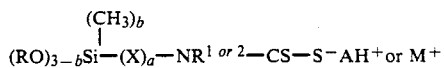

are isolated and combined with at least the equimolar amount of an amino compound of the general formula

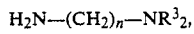

this mixture is heated until the reaction is completed and the desired product is subsequently isolated.

3 Claims, 3 Drawing Sheets

N,N'-DISUBSTITUTED AND N,N,N'-/N,N', N'-TRISUBSTITUTED THIOUREAS AND METHOD OF THEIR PREPARATION (II)

The present invention relates to N,N'-disubstituted and N,N,N' or N,N',N'-trisubstituted thioureas with, in addition, at least one hydrolyzable silyl group and at least one tertiary amino function. The invention also relates to a method of preparing these compounds.

BACKGROUND OF THE INVENTION

A. Baigozhin, Zh. Obshch. Khim. 43 (1973), 1408 (C.A. 79:66463r) describes the reaction of aminopropyltrialkoxysilanes with alkylisothiocyanates which results in N,N'-disubstituted thioureas of the formula (RO)$_3$Si—(CH$_2$)$_3$—NH—CS—NH—R' in which R=ethyl and R'=phenyl or allyl. These compounds are used for the modification of silicon-containing polymers and coatings.

A symmetrical N,N'-substituted compound is described by M. G. Voronkov et al. in Zh. Obshch. Khim, 54 (1984), 1098 (C.A. 101:192031j). It is obtained by reacting aminopropyltrialkoxysilanes with thiourea ((RO)$_3$Si—(CH$_2$)$_3$—NH—CS—NH—(CH$_2$)$_3$—Si(OR)$_3$).

Published German Patent Application DE-OS 38 21 465 describes di- or polysubstituted organyloxysilyl-functional thioureas.

None of the compounds cited in the three publications mentioned has a further reactive group such as e.g. an amine group in addition to the hydrolyzable silyl group and the thiourea function.

SUMMARY OF THE INVENTION

The object of the present invention is to provide novel, N,N'-disubstituted and N,N,N' or N, N',N'-trisubstituted organyloxysilyl-functional thioureas which additionally comprise a tertiary amine function. A further object of the present invention is to provide a method of preparing these compounds.

In accordance with the present invention, there are provided N,N'-disubstituted or N,N,N'- or N, N',N'-trisubstituted thioureas of the general formula:

$$\overset{(CH_3)_b}{(RO)_{3-b}-Si-(X)_a-NR^1-CS-NR^2-(CH_2)_n-NR_2^3} \quad (I)$$

in which
b is 0, 1 or 2
R is alkyl with 1 to 6 carbon atoms, cycloalkyl with 5 to 7 carbon atoms, aryl or aralkyl
X is —CH$_2$—if a=1, 3, 4, 5 or 6, or
X is

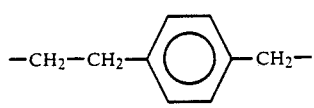

if a=1,
R$^1$ and R$^2$ are both equal to hydrogen, or
R$^1$ is hydrogen and R$^2$ is

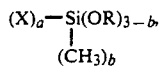

or

R$^1$ is

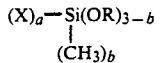

or (CH$_2$)$_n$—NR$_2^3$ and R$^2$ is hydrogen
R$^3$ is alkyl with 1 to 3 carbon atoms, and
n is 1 to 6.

Compounds are preferred in which:
R is alkyl with 1 to 3 carbon atoms,
X is —CH$_2$—,
a is 3,
b is 0,
R$^3$ is methyl or ethyl, and
n is 2 or 3.

The invention also provides a method of preparing the N,N'-disubstituted and N,N,N'- or N,N',N'-trisubstituted organyloxysilyl- and tertiary amine-functional thioureas of Formula I which method is characterized in that:

a) Amino-organylsilanes of the general formula:

$$\overset{(CH_3)_b}{(RO)_{3-b}Si-(X)_a-NHR^{1 \, or \, 2}} \quad (II)$$

in which a, b, X, R, R$^1$ and R$^2$ have the meanings given above are reacted in an organic, inert solvent with carbon disulfide, optionally with cooling. The reaction takes place using compounds according to Formula (II) in the presence of a tertiary amine (A) or alkali alcoholate (MOR), b) The dithiocarbamates formed thereby have the general formula:

$$\overset{(CH_3)_b}{(RO)_{3-b}Si-(X)_a-NR^{1 \, or \, 2}-CS-S^{\ominus}AH^{\oplus} \, or \, M^{\oplus}} \quad (III)$$

These dithiocarbamates are isolated and mixed with at least an equimolar amount of an amino compound of the general formula:

H$_2$N—(CH$_2$)$_n$—NR$_2^3$ (IV)

in which R, R$^1$, R$^2$, R$^3$, a, b, X and n have the meanings given above. This mixture is heated until the reaction is concluded and the desired product of Formula I is subsequently isolated using known methods.

Compounds are preferred in which —(X)$_a$— stands for —(CH$_2$)$_3$—.

The preparation of the desired compounds takes place in accordance with the method schemes presented by way of example in the following:

(C$_2$H$_5$O)$_3$Si—(CH$_2$)$_3$—NH$_2$ + CS$_2$ + N(C$_2$H$_5$)$_3$

↓ THF/Pentane

-continued

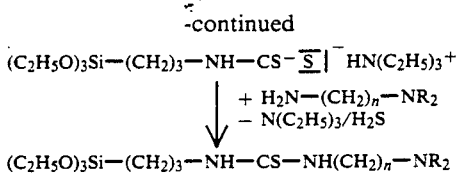

Reaction scheme 1: Preparation of N,N'-disubstituted thioureas with a hydrolyzable silyl group and a tertiary amine function.

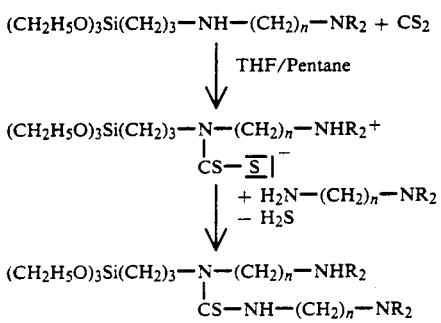

Reaction scheme 2: Preparation of N,N,N'-trisubstituted thioureas with a hydrolyzable silyl group and two tertiary amine functions.

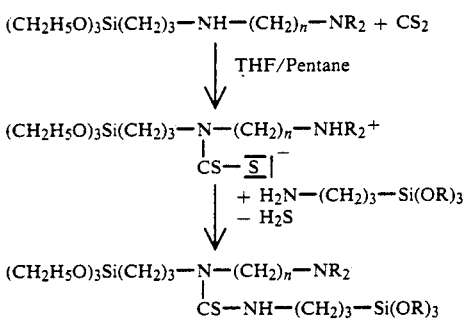

Reaction scheme 3: Preparation of N,N,N'-trisubstituted thioureas with two hydrolyzable silyl groups and one tertiary amine function.

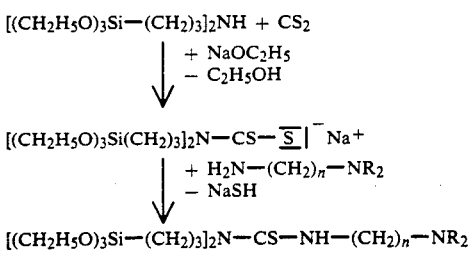

Scheme 4: Preparation of N,N,N'-trisubstituted thioureas with two hydrolyzable silyl groups and one tertiary amine function.

The amine-functional starting materials 3 can be prepared by the method of J. L. Speier et al., J. Org. Chem. 36 (1971), pp. 3120 ff., e.g. from chloroalkylsilanes and diamines.

The reaction steps for preparing dithiocarbamates 1, 4, and 7 are preferably carried out in a non-polar, aprotic solvent if tertiary amines are used as the proton acceptor. Particularly suitable solvents are (halogenated) hydrocarbons or (cyclic) ethers such as e.g. n-pentane or tetrahydrofuran as well as their mixtures. If an alkali alcoholate is used as proton acceptor, then polar, aprotic solvents such as e.g. dimethylformamide and also certain polar, protic solvents such as e.g. alcohols are also suitable. It is especially advantageous in the latter instance to prepare the alkali alcoholate directly by means of the reaction of alkali metal, especially sodium or potassium, with an alcohol, especially methanol or ethanol, according to known methods and to use this reaction solution directly for the reaction to dithiocarbamate.

An essential prerequisite for the suitability as solvent is the fact that it must, on the one hand, dissolve the aminosilane starting material while, on the other hand, the dithiocarbamate formed should be precipitated a quantitatively as possible. The solvent should also be inert. The reactants aminoorganylsilane, carbon disulfide and the required proton acceptor (tertiary amine or alkali alcoholate) are used in a molar ratio of approximately 1:1, but a deviation of up to 10 % from the stoichiometrically required amounts are permissible.

The reactions, which begin immediately upon mixing the reactants, with formation of dithiocarbamates 1, 4 or 7, are preferably carried out at temperatures below the boiling point of the carbon disulfide, especially at temperatures from 0° to 46° C. The silicon-organic compound is added with advantage to the carbon disulfide, which can be present in a reaction vessel in a stoichiometric excess. The precipitated "dithiocarbamate" is filtered off and freed from the solvent residues under a vacuum.

Dithiocarbamates such as those obtained via the Reactions schemes 1 to 4 as intermediates are partially known from the literature. However, according to the state of the art, they are used for reaction with acrylonitrile (see Published German Patent Application DE-OS 20 00 224) or converted by hydrolysis into polysiloxane compounds (see U.S. Pat. No. 2,938,046).

According to the invention, the "dithiocarbamates" accumulating as bright yellow crystal powders are reacted to form thioureas. According to Reaction schemes 1 to 4, primary amines are preferably heated for this purpose in equimolar mixtures with the organosilicon compounds in general without addition of solvent, but with agitation, at temperatures of 80° to 140° C. with formation of thioureas 2, 5, 6 or 8.

In an advantageous embodiment (cf. Published German Patent Application DE-OS 38 21 465) the hydrogen sulfide which develops as a by-product, and the tertiary amine which splits off when ammonium dithiocarbamates are used, are drawn off under a vacuum. The thioureas, which accumulate in high yields in the form of viscous, colored liquids, do not need to be purified further.

If an alkali dithiocarbamate is used in this reaction, then no hydrogen sulfide is produced but rather the corresponding alkali hydrogen sulfide is formed. The latter is separated from the desired product by means of precipitation with a suitable solvent, e.g. acetone, in accordance with current workup methods.

The compounds of the invention are used after heterogenization in themselves for the removal of metal ions (especially Cu(II)) from aqueous and non-aqueous media, which takes place via the amine and thiourea groups with a chelate-complexing action.

The compounds may be used by dissolving them in a non-miscible organic solvent such as kerosene and intimately mixing them with an aqueous solution of a copper salt. Copper can then be recovered by separating the organic solvent solution from the aqueous solution and intimately mixing the organic solvent solution with an aqueous acid solution.

The exact description can be gathered from German Patent Applications P 39 25 357.0, 39 25 358.9, 39 25 359.7 and P 39 25 360.0.

DETAILED DESCRIPTION OF PREFERRED EMBODIMENTS

The following general procedure is used for preparing thioureas of Formula 2 in Examples 1–3:

Equimolar amounts of ammonium dithiocarbamate 1 (preparation cf. DE-OS 38 21 465, Example 2) and of an N,N-dialkylalkylene diamine are heated in a glass flask equipped with a distillation head, with agitation, at normal pressure, for 2 hours to 120° C., during which time the triethylamine being released is distilled off. In order to remove the last residues of amine and hydrogen sulfide, the liquid reaction product obtained is subjected for an additional 30 minutes to a reduced pressure of 1 mbar at a temperature of 100° C.

EXAMPLE 1

[N-2-(dimethylamino)ethyl-N'-3-(triethoxysilyl)propyl] thiourea

Preparation from 199.3 g compound of Formula 1 (0.5 mole) and 44.1 g N,N-dimethylethylene diamine (0.5 mole);

Yield: 169.7 corresponding to 96.5% of theory; yellowish-brown viscous liquid;

| $C_{14}H_{33}N_3O_3SSi$ | (351.586) | | | |
|---|---|---|---|---|
| | C[%] | H[%] | N[%] | S[%] |
| Calculated: | 47.83 | 9.46 | 11.95 | 9.12 |
| Observed: | 46.8 | 9.6 | 12.3 | 9.8 |

Figure 1:
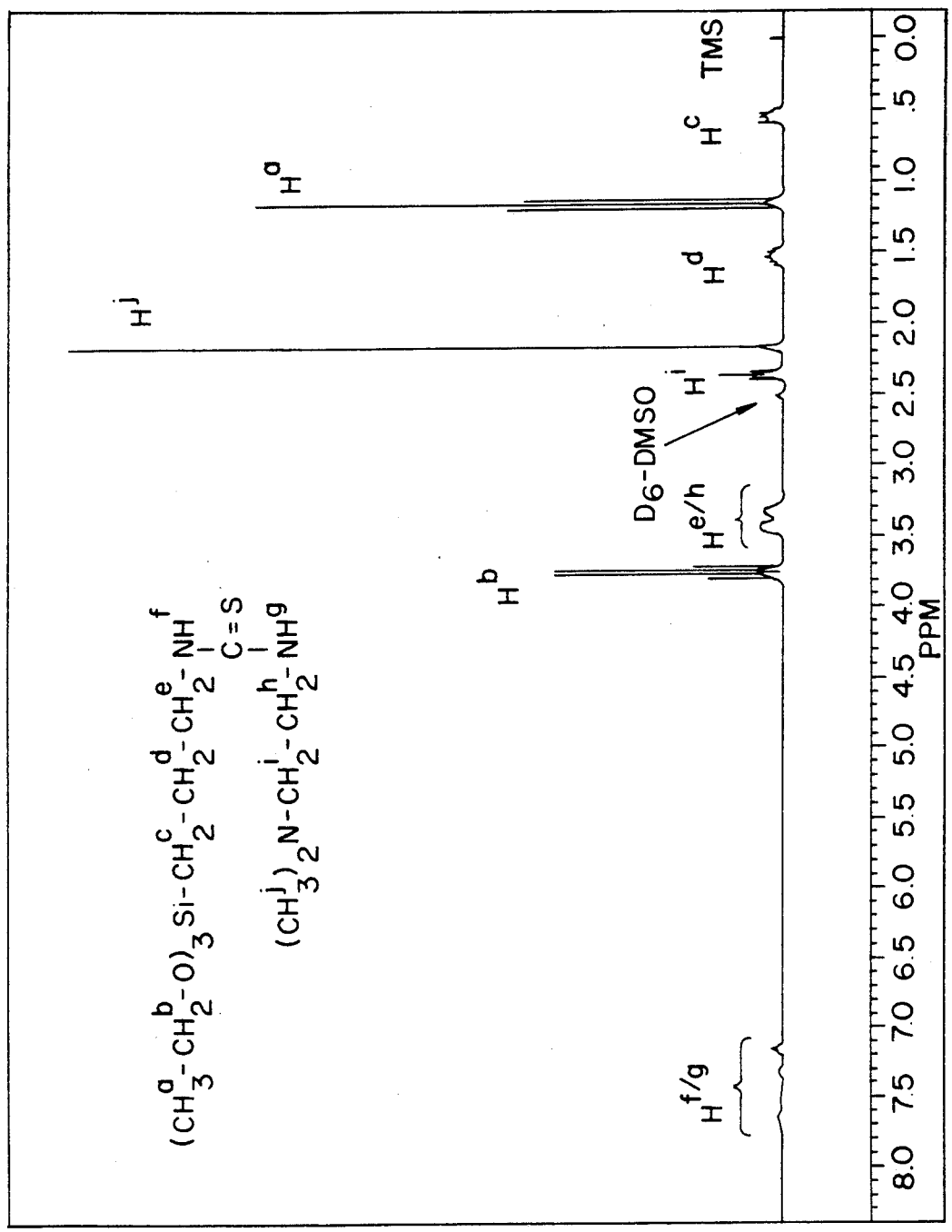

The IH-NMR spectrum (250 MHz) of this thiourea is reproduced in FIG. 1.

EXAMPLE 2

[N-2-(diethylamino)ethyl-N'-3-(triethoxysilyl) propyl] thiourea

Preparation from 199.3 g compound of Formula 1 (0.5 mole) and 58.1 g N,N-diethylethylene diamine (0.5 mole);

Yield: 186 g corresponding to 98.0% of theory; orange yellow, viscous liquid;

| $C_{16}H_{37}N_3O_3SSi$ | (379.640) | | | |
|---|---|---|---|---|
| | C[%] | H[%] | N[%] | S[%] |
| Calculated: | 50.62 | 9.82 | 11.07 | 8.45 |
| Observed: | 49.9 | 10.5 | 11.2 | 8.1 |

EXAMPLE 3

[N-3-(dimethylamino)propyl-N'-3-(triethoxysilyl) propyl] thiourea

Preparation from 210.2 g compound of Formula 1 (0.53 mole) and 53.9 g N,N-dimethyltrimethylene diamine (0.53 mole);

Yield: 183 g corresponding to 95.5% of theory; yellowish brown, viscous liquid;

| $C_{15}H_{35}N_3O_3SSi$ | (365.613) | | | |
|---|---|---|---|---|
| | C[%] | H[%] | N[%] | S[%] |
| Calculated: | 49.28 | 9.65 | 11.49 | 8.77 |
| Observed: | 48.1 | 10.0 | 11.4 | 9.2 |

The following procedure is used for preparing dithiocarbamates 4 in Examples 4–8.

1.1 mole carbon disulfide in THF as solvent (350 ml per mole $CS_2$) are placed in a receiver per mole silane of Formula 3 to be used (preparation cf. J. Org. Chem. 36 (1971), 3120). The silane 3 is added into the receiver, with external cooling with ice, at such a rate that the temperature of the reaction mixture remains below 25° C. The respective dithiocarbamates 4 precipitate in the form of yellowish solids during the addition of silane. In order to complete the precipitation, the mixture is mixed with petroleum ether (approximately 1.5 liters per mole 3) after the end of the addition of 3. The precipitated product is separated from solvent by means of filtration and drying in a vacuum and does not need to be purified further for subsequent reactions.

EXAMPLE 4

[N-2-(dimethylamino)ethyl-N-3-(triethoxysilyl) propyl] dithiocarbamate

Preparation from 35.8 g $CS_2$ (0.47 mole, excess) and 125.0 g [N,N-dimethyl-N'-(triethoxysilyl)propyl] ethylene diamine (0.43 mole);

Yield: 150 g corresponding to 95.8% of theory; bright yellow powder.

EXAMPLE 5

[N-2-(diethylamino)ethyl-N-3-(triethoxysilyl) propyl] dithiocarbamate

Preparation from 41.9 g $CS_2$ (0.55 mole, excess) and 160.3 g (N,N-diethyl-N'-3-(triethoxysilyl) propyl] ethylene diamine (0.5 mole);

Yield: 179.4 g corresponding to 90.4% of theory; bright yellow powder.

EXAMPLE 6

[N-3-(dimethylamino) propyl-N-3-(triethoxysilyl) propyl] dithiocarbamate

Preparation from 41.9 g $CS_2$ (0.55 mole, excess) and 153.3 g [N,N-dimethyl-N'-3-(triethoxysilyl) propyl] trimethylene diamine (0.5 mole);

Yield: 159.3 g corresponding to 83.2% of theory; bright yellow crystal powder.

The following procedure is used for preparing silylalkylthioureas of Formula 5 in Examples 7–8:

Equimolar amounts of N,N-dialkylalkylene diamine and dithiocarbamate of Formula 4 are mixed and heated for 2.5 hours to 120° C., during which time the desired products are formed with constant release of hydrogen sulfide. Residual amounts of physically dissolved $H_2S$ are subsequently removed by vacuum.

EXAMPLE 7

[N-2-(diethylamino)ethyl-N'-2-(diethylamino)ethyl-N'-3-(triethoxysilyl) propyl] thiourea Preparation from 52.2 g N,N-diethylethylene diamine (0.45 mole) and 178 g [N-2-(diethylamino)ethyl-N-3-(triethoxysilyl) propyl] dithiocarbamate from Example 5 (0.45 mole)

Yield: 208.9 g corresponding to 97.0% of theory; orange-colored, viscous liquid;

| $C_{22}H_{50}N_4O_3SSi$ | (478.817) | | | |
|---|---|---|---|---|
| | C[%] | H[%] | N[%] | S[%] |
| Calculated: | 55.19 | 10.53 | 11.70 | 6.70 |
| Observed: | 55.0 | 10.6 | 11.7 | 6.94 |

Figure 2:
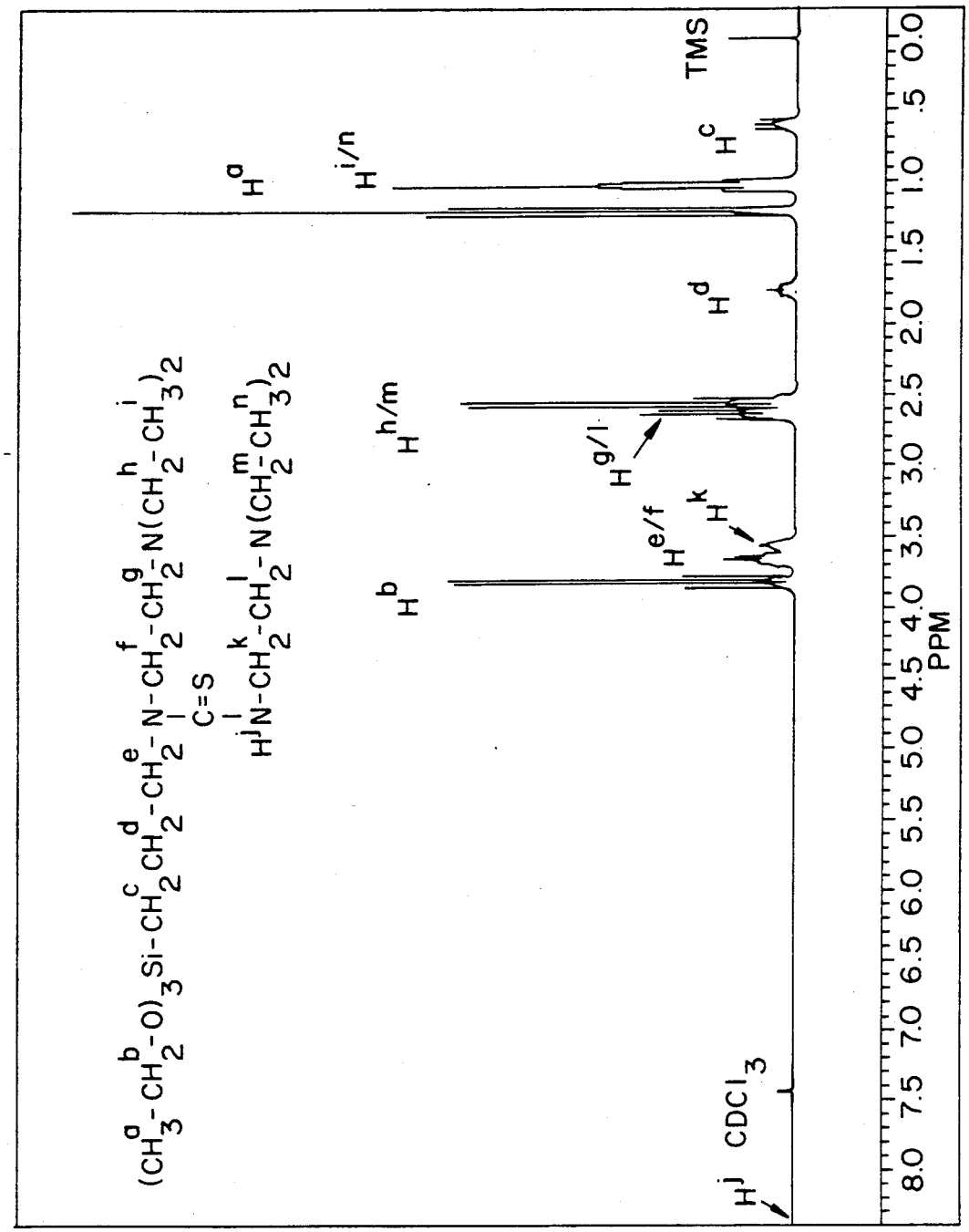

The 1H-NMR spectrum (250 MHz) of this thiourea is reproduced in FIG. 2.

EXAMPLE 8

N-3-(dimethylamino)propyl-N'-3-(dimethylamino)propyl-N'-3-(triethoxysilyl) propyl] thiourea Preparation from 41.9 g N,N-dimethyltrimethylene diamine (0.41 mole) and 158.1 g [N-3-(dimethylamino)-propyl-N-3-(triethoxysilyl) propyl] dithiocarbamate from Example 6

Yield: 175.5 g corresponding to 95.0% of theory; orange-colored, viscous liquid;

| $C_{20}H_{46}N_4O_3SSi$ | (450.763) | | | |
|---|---|---|---|---|
| | C[%] | H[%] | N[%] | S[%] |
| Calculated: | 53.29 | 10.29 | 12.43 | 7.11 |
| Observed: | 52.8 | 10.8 | 12.9 | 8.0 |

The following procedure was used for preparing bis(silylalkyl) thioureas of general Formula 6 in Examples 9–10:

Equimolar amounts of diamine-functional silane of Formula 3 and ammonium dithiocarbamate of Formula 1 are mixed and agitated for 1 hour at a temperature of 120° C. and a reduced pressure of approximately 100 mbar. The mixture of triethylamine and hydrogen sulfide formed at a temperature of approximately 70° C. is condensed in a cold trap and the condensate can be worked up according to methods customary to the triethylamine required for preparing the compound of Formula 1. In order to eliminate the last remnants of volatile components, the pressure is finally reduced for approximately 10 min. to 1 mbar.

EXAMPLE 9

[N-3-(triethoxysilyl)propyl-N'-2-(dimethylamino) ethyl-N'-3-(triethoxysilyl) propyl] thiourea:

Preparation from 131.6 g [N,N-dimethyl-N'-3-(triethoxysilyl) propyl] ethylene diamine (0.45 mole) and 179.4 g 1 (0.45 mole);

Yield: 246.5 g corresponding to 98.5% of theory; reddish brown, viscous liquid;

| $C_{23}H_{53}N_3O_6SSi_2$ | (555.928) | | | |
|---|---|---|---|---|
| | C[%] | H[%] | N[%] | S[%] |
| Calculated: | 49.69 | 9.61 | 7.56 | 5.77 |
| Observed: | 49.1 | 10.2 | 7.7 | 6.1 |

Figure 3:
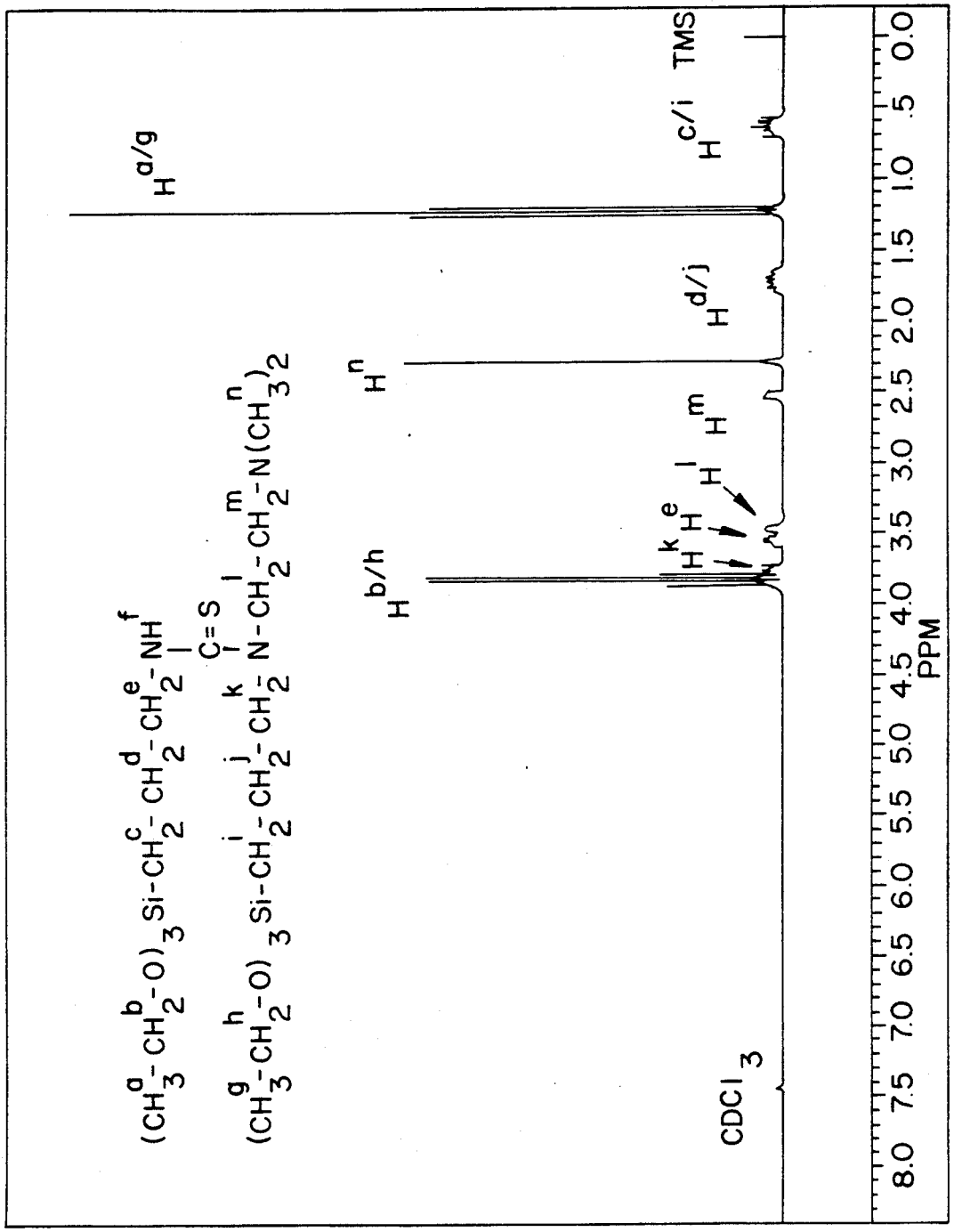

The 1H-NMR spectrum (250 MHz) of this thiourea is reproduced in FIG. 3.

EXAMPLE 10

[N-3-(triethoxysilyl)propyl-N'-2-(diethylamino) ethyl-N'-3-(triethoxysilyl) propyl] thiourea:

Preparation from 115.4 g [N,N-diethyl-N'-3-(triethoxysilyl)propyl] ethylene diamine (0.36 mole) and 144.1 g 1 (0.36 mole);

Yield: 209.0 g corresponding to 99.4% of theory; yellowish brown, viscous liquid;

| $C_{25}H_{57}N_3O_6SSi_2$ | (583.982) | | | |
|---|---|---|---|---|
| | C[%] | H[%] | N[%] | S[%] |
| Calculated: | 51.42 | 9.84 | 7.20 | 5.49 |
| Observed: | 50.3 | 10.4 | 7.1 | 6.4 |

The following procedure is used in Example 11 for preparing bis(silylalkyl) thioureas of general Formula 8:

In order to prepare the required sodium dithiocarbamate intermediate of Formula 7, a mixture consisting of bis(3-triethoxysilylpropyl) amine (1 mole per mole Na) carbon disulfide (1.1 mole per mole Na) and ethanol (300 ml per mole Na) are added so slowly under external cooling into a solution of sodium ethoxide (obtained by adding elementary sodium to ethanol—500 ml per mole Na) that the temperature of the reaction mixture does not exceed a value of 30° C. After the solvent is drawn off, the sodium dithiocarbamate 7 is obtained in the form of a highly viscous, yellow liquid in practically quantitative yield.

EXAMPLE 11

| $C_{19}H_{42}NNaO_6S_2Si_2$ | (523.836) | | | |
|---|---|---|---|---|
| | C[%] | H[%] | N[%] | S[%] |
| Calculated: | 43.57 | 8.08 | 2.67 | 12.24 |
| Observed: | 43.4 | 8.3 | 2.4 | 12.5 |

The following procedure is used in Example 12:

Equimolar amounts of sodium dithiocarbamate 7 and N,N-dialkylalkylene diamine are mixed and agitated for 2 hours at a temperature of 140° C. (if necessary, with refluxing of the diamine, which can be used in excess). After the mixture has cooled, it is combined with acetone (1.5 liters per mole 7) and filtered to separate the precipitated sodium hydrogen sulfide. Volatile components (solvent, perhaps excess of diamine) are subsequently removed in a vacuum.

EXAMPLE 11

(N,N-bis[3-(triethoxysilyl)propyl]-N'-3-(dimethylamino) propyl) thiourea

Preparation from 262 g 7 (0.5 mole) and 51.1 g N,N-dimethyltrimethylene diamine;

Yield: 269.5 g corresponding to 94.6% of theory; yellow, viscous liquid;

| $C_{24}H_{55}N_3O_6SSi_2$ | (569.995) | | | |
|---|---|---|---|---|
| | C[%] | H[%] | N[%] | S[%] |
| Calculated: | 50.58 | 9.73 | 7.37 | 5.63 |
| Observed: | 49.1 | 9.1 | 7.5 | 7.0 |

What is claimed is:

1. N,N'-disubstituted and N,N,N'-or N, N',N'-trisubstituted thioureas with additional organyloxysilyl function and tertiary amine function of the general formula

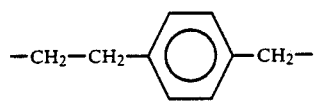

in which
b is 0, 1 or 2
R is alkyl with 1 to 6 carbon atoms, cycloalkyl with 5 to 7 C atoms, aryl or aralkyl
X is —CH$_2$— if a=1, 3, 4, 5 or 6, or
X is

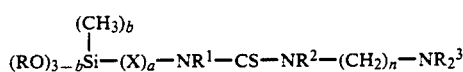

if a=1,
R$^1$ and R$^2$ are hydrogen, or
R$^1$ is hydrogen and
R$^2$ is

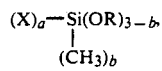

or R$^1$ is

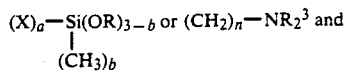

R$^2$ is hydrogen,
R$^3$ is alkyl with 1 to 3 C atoms
n is 1 to 6.
2. Compounds as set forth in claim 1 in which
R is alkyl with 1 to 3 carbon atoms,
X is —CH$_2$—,
a is 3,
b is 0,
R$^3$ is methyl or ethyl, and n is 2 or 3.
3. Compounds as set forth in claim 1 in which (X)$_a$ is —(CH$_2$)$_3$—.

* * * * *